United States Patent
Ramirez (10) Patent No.: US 10,792,171 B2
(45) Date of Patent: Oct. 6, 2020

(54) PROSTHETIC ADAPTER MODULE

(71) Applicant: FILLAUER EUROPE AB, Sollentuna (SE)

(72) Inventor: Christoffer Ramirez, Vallentuna (SE)

(73) Assignee: Fillauer Europe AB, Sollentuna (SE)

( * ) Notice: Subject to any disclaimer, the term of this patent is extended or adjusted under 35 U.S.C. 154(b) by 105 days.

(21) Appl. No.: 16/075,254

(22) PCT Filed: Jan. 25, 2017

(86) PCT No.: PCT/SE2017/050066
§ 371 (c)(1),
(2) Date: Aug. 3, 2018

(87) PCT Pub. No.: WO2017/135868
PCT Pub. Date: Aug. 10, 2017

(65) Prior Publication Data
US 2019/0046337 A1   Feb. 14, 2019

(30) Foreign Application Priority Data

Feb. 5, 2016  (SE) .................................... 1650145-4

(51) Int. Cl.
*A61F 2/76* (2006.01)
*A61F 2/60* (2006.01)
(Continued)

(52) U.S. Cl.
CPC .................. *A61F 2/76* (2013.01); *A61F 2/60* (2013.01); *A61F 2/6607* (2013.01); *A61F 2/80* (2013.01);
(Continued)

(58) Field of Classification Search
CPC ...... A61F 2/78; A61F 2/76; A61F 2/80; A61F 2/60; A61F 2/601; A61F 2002/7887;
(Continued)

(56) References Cited

U.S. PATENT DOCUMENTS

| 5,013,325 A | 5/1991 | Rennerfelt |
| 5,443,526 A | 8/1995 | Hoerner |

(Continued)

FOREIGN PATENT DOCUMENTS

| DE | 203 13 997 U1 | 12/2003 |
| EP | 1 017 340 B1 | 4/2004 |
| WO | 93/17640 | 9/1993 |

OTHER PUBLICATIONS

Extended European Search Report for corresponding European Patent Application No. 17747869.0 dated Sep. 10, 2019.
(Continued)

*Primary Examiner* — Brian A Dukert
*Assistant Examiner* — Amanda M Barkan
(74) *Attorney, Agent, or Firm* — Renner, Otto, Boisselle & Sklar, LLP (57) ABSTRACT

An adapter module (2) configured to be attached, by a predetermined number of screws (4), to a socket member (6) of a prosthetic sleeve (8), into which sleeve (8) an amputation stump of a prosthesis user is to be inserted. The adapter module (2) comprises a module body (10) provided with a washer space (12) structured to provide room for a disc-shaped connection washer (14), the washer space (12) has an extension to provide for movement of the connection washer (14) within a plane essentially perpendicular to a longitudinal axis A of said prosthetic sleeve (8) prior the connection washer (14) is fixated in a determined position. The connection washer (14) is provided with a through-going first opening (16) structured to receive a washer attachment screw (18) such that the screw essentially extends along said longitudinal axis A. The through-going first opening (16) is preferably positioned off-centered of the washer (14) in order to maximize movement of the washer in all directions within the plane.

9 Claims, 6 Drawing Sheets (51) Int. Cl.
*A61F 2/66* (2006.01)
*A61F 2/80* (2006.01)
*A61F 2/50* (2006.01)

(52) U.S. Cl.
CPC ................. *A61F 2002/5018* (2013.01); *A61F 2002/5023* (2013.01)

(58) Field of Classification Search
CPC ........ A61F 2002/607; A61F 2002/6614; A61F 2002/5018; A61F 2002/5021; A61F 2002/5023
See application file for complete search history.

(56) References Cited

U.S. PATENT DOCUMENTS

| | | | |
|---|---|---|---|
| 6,013,105 A | 1/2000 | Potts | |
| 2012/0259433 A1* | 10/2012 | Dillingham | A61F 2/78 623/36 |
| 2015/0012113 A1 | 1/2015 | Celebi | |
| 2015/0164659 A1* | 6/2015 | Konishi | A61F 2/76 623/27 |

OTHER PUBLICATIONS

International Search Report and Written Opinion for corresponding Patent Application No. PCT/SE2017/050066 dated Mar. 31, 2017.

* cited by examiner

FIG. 1

-- PRIOR ART --

FIG. 2

-- PRIOR ART --

PROSTHETIC ADAPTER MODULE

This application is a national phase of International Application No. PCT/SE2017/050066 filed 25 Jan. 2017 and published in the English language, which claims priority to Swedish Patent Application No. 1650145-4 filed Feb. 5, 2016, which are hereby incorporated herein by reference.

TECHNICAL FIELD

The present disclosure relates to a prosthetic adapter module configured to be attached to a socket member of a prosthetic sleeve to be used to connect a prosthetic limb device, e.g. a leg, a foot or an arm. The present disclosure also relates to a prosthetic arrangement comprising a prosthetic adapter module and an angle adjustment module.

BACKGROUND

A user of prosthesis normally inserts the amputation stump into a soft sleeve. Thereafter the amputation stump with the soft sleeve is inserted into a rigid prosthetic sleeve, and the soft sleeve is firmly fixated inside the rigid sleeve either mechanically or by under pressure created between the sleeves.

It is extremely imported for the amputee to have an optimally adjusted prosthesis as it determines if the user may or may not use the prosthesis. All users are different, and all users change over time. Therefore, the prosthesis must be able to be continuously adjusted, and all prosthesis must be individually adjusted to each person using it.

There exist various solutions for providing attachments of artificial limbs. Such devices are generally built with a socket member fixated to a prosthetic sleeve into which sleeve the stump of the leg or arm is inserted. The artificial limb including e.g. a tube is then attached to the sleeve via the socket member.

To ensure a proper position of the artificial limb and its parts the attachment between the socket member and tube needs to allow translatory and angular displacement so that the amputee can achieve the highest possible gait efficiency.

In U.S. Pat. No. 5,013,325 is disclosed a device that via an adjustment head arranged at the upper end of the tube allows setting of the angular position of the tube relative to an imagined load line. Other means are provided to allow a translatory displacement of the tube relative to the adjustment head. Adjustment means allow a basic adjustment of the tube when having the prosthesis fitted. This device requires the attachment point to be permanently fixed in the socket, thus limiting its use to those specific socket designs.

Additionally in U.S. Pat. No. 3,659,294 is shown an adjustable connection between two members of an artificial leg or arm, or the like. This device demonstrates a square stud having the form of a cut four sided pyramid, divergently extending from the base. The device only permits an angular adjustment in two defined planes relative to the socket but no translatory adjustment of the kind achieved according to U.S. Pat. No. 5,013,325.

U.S. Pat. No. 5,163,965 discloses a socket design including an attachment plate with four screw holes to attach a pyramidal connector or similar to attach a variety of other adapters to achieve an angular alignment. The translatory adjustment is lacking.

In U.S. Pat. No. 5,888,233 is disclosed an arrangement for leg prosthesis provided with an adjustment head to attach an elongated member of an artificial leg to a prosthetic leg. An adjustment device is provided to perform translatory adjustments of a pyramid adapter stud. More in detail the adjustment device comprises an upper washer arranged above a supporting plate that is provided with a hole.

One drawback with the solutions presented in U.S. Pat. Nos. 5,888,233 and 5,013,325 is that the lower connection part of the prosthetic sleeve is provided with a through-going hole, which results in that the prosthetic sleeve to be attached to the amputation stump is not air tight which in its turn results in that the prosthetic sleeve may not be properly attached to the amputation stump via under pressure.

One object with the present invention is to remove the drawbacks of the prior art technique and to achieve a prosthesis that easily may be adjusted with regard to angles, and with regard to positions in a plane perpendicular to a longitudinal axis of the prosthetic sleeve. One particular object is to achieve an adapter module that facilitates these adjustments without having to take off the prosthesis.

SUMMARY

The above-mentioned objects are achieved by the present invention according to the independent claims.

Preferred embodiments are set forth in the dependent claims.

The present invention relates to an adapter module for use in creating artificial limbs that utilize a standardized attachment point to a socket member of a prosthetic sleeve.

The adapter module gives the practitioner the possibility to align the socket member with the chosen prosthetic components, in a wider range than previously possible. Instead of just having an angle adjustment possible the practitioner can, with the adapter module according to the present invention, utilize several other attachment methods and systems, while also getting the option to adjust the translatory position.

In a further aspect of the present invention a prosthetic arrangement is provided comprising the adapter module and an angle adjustment module connected to the adapter module with an attachment screw. The adapter module makes it possible to make adjustments both in a plane perpendicular to an axis A of the prosthetic sleeve, and rotational adjustments around axis A, and the angle adjustment module provides for angle adjustments in the sagittal and frontal planes. Thus, all adjustments may be performed essentially at the same place.

The adapter module is preferably made from a material having low weight and is structured to be attached close to the socket member of the rigid sleeve. This reduces the inertia and improves the mobility of the user movement of the prosthesis.

DETAILED DESCRIPTION

The adapter module will now be described in detail with references to the appended figures. Throughout the figures the same, or similar, items have the same reference signs. Moreover, the items and the figures are not necessarily to scale, emphasis instead being placed upon illustrating the principles of the invention.

Figure 1:
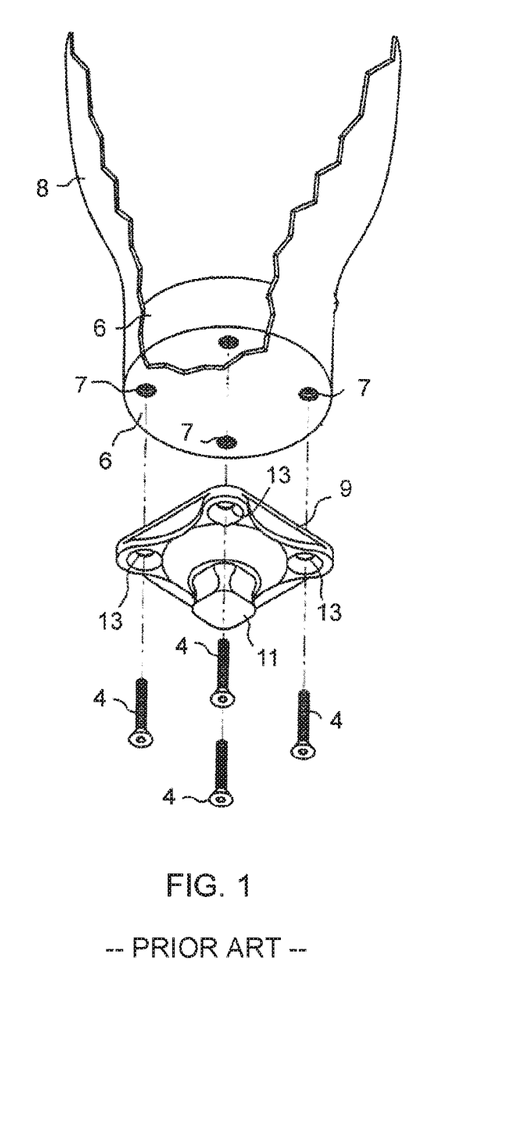
FIG. 1 shows a schematic illustration of a prior art prosthetic sleeve provided with a socket member having four holes, and a standard pyramidal attachment plate to be mounted at the for the four hole socket member.

FIG. 1 shows a schematic illustration of a prior art prosthetic sleeve 8 provided with a socket member 6 having four holes 7, and a standard pyramidal attachment plate 9 to be mounted at the four hole socket member 6, and provided with a square stud 11 having the form of a cut four sided pyramid, divergently extending from the base, and four screw holes 13.

Figure 2:
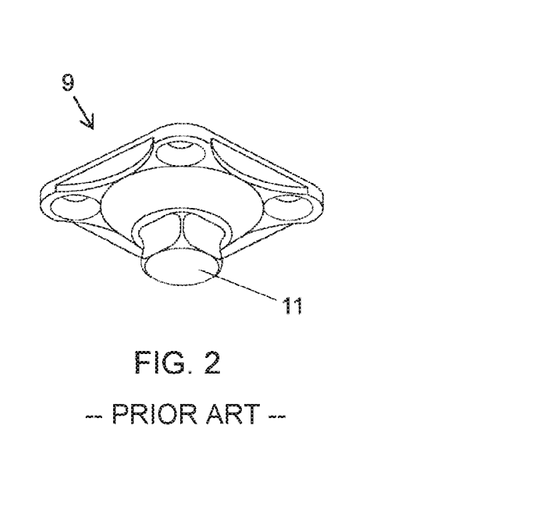
FIG. 2 shows a prior art standard pyramidal attachment plate for the four hole socket member.

FIG. 2 shows the prior art standard pyramidal attachment plate 9 for the four hole socket member 6.

An adapter module is provided that is configured to be attached to the fixed socket member of the sleeve by a predetermined number of screws, preferably four screws that securely attach the adapter module to the socket member and thus the amputation stump. The adapter module is thus oriented to facilitate translation into all direction within a plane which is approximately perpendicular to the longitudinal axis of the amputation stump.

Figure 4:
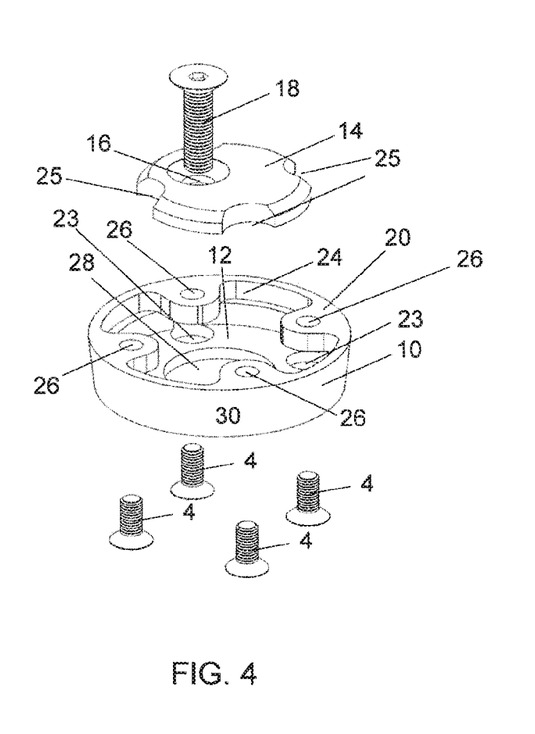
FIG. 4 illustrates the individual components of the adapter module.
Figure 5:
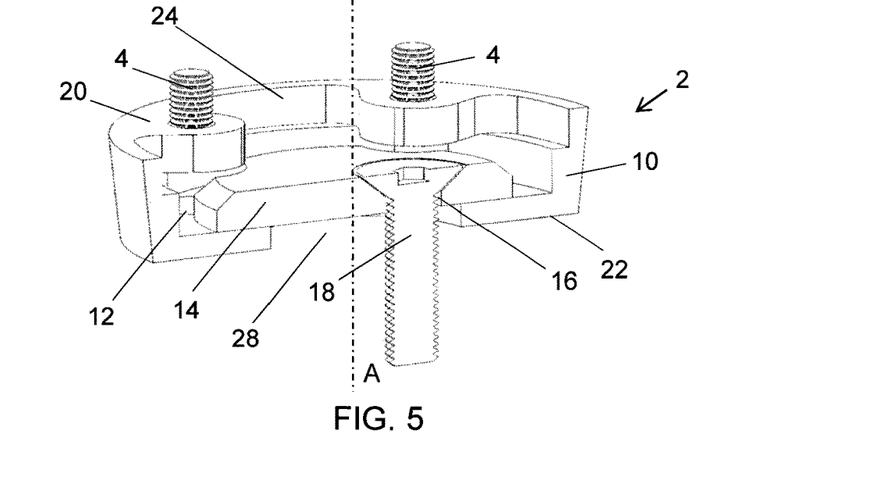
FIG. 5 shows a cross-sectional view of the adapter module.

First with references to FIGS. 3-5, the adapter module 2 will be described in detail. The adapter module is configured to be attached, by a predetermined number of screws 4, e.g. four, to a socket member 6 (see FIG. 1) of a prosthetic sleeve 8 (see FIG. 1), into which sleeve 8 an amputation stump of a prosthesis user is to be inserted and attached e.g. mechanically or by under pressure.

The adapter module 2 comprises a module body 10 provided with a washer space 12 structured to provide room for a disc-shaped connection washer 14. The module body is preferably made from a high-strength and light-weight material. The washer space 12 has an extension to provide for movement of the connection washer 14 within a plane essentially perpendicular to a longitudinal axis A of the prosthetic sleeve 8 prior the connection washer 14 is fixated in a determined position.

The connection washer 14 is provided with a through-going first opening 16 structured to receive a washer attachment screw 18 such that the screw essentially extends along the longitudinal axis A. Preferably the attachment screw is oriented as illustrated in the figures such that the threaded end is in a direction away from the amputation stump.

As an alternative, the through-going first opening 16 may be provided with threads. In that case the attachment screw is oppositely directed in comparison to the illustrated embodiments.

The through-going first opening 16 is preferably positioned off-centered of the washer 14 in order to maximize movement of the washer in all directions within the plane.

The module body 12 is provided with a first side 20 structured to face the socket member 6, and a second side 22 at the other side of the module body. The first side 20 is provided with a second opening 24 giving access to the washer space 12 and having a size such that the washer 14 may enter the washer space 12 via the second opening 24.

The first side 20 is provided with a predetermined number of through-going holes 26 structured to receive the screws 4 for attachment of the adapter module 2 to the socket member 6 of the prosthetic sleeve.

The second side 22 of the module body is provided with a through-going third opening 28 through which opening the washer attachment screw 18 extends. The third opening 28 is essentially circular and has a width in a direction perpendicular to the longitudinal axis of the screw 18 that is larger than the outer diameter of the screw, but smaller than the diameter of the disc-shaped connection washer 14. Thereby the washer may be moved in its plane in order to obtain a position for the attachment screw 18 such that the loads the prosthesis are subjected to may be optimally transferred to the user of the prosthesis.

The second side 22 is further provided with openings 23 to give access to the screws 4 used to connect the adapter module to the socket member 6.

The connection washer 14 is preferably provided with indentations 25 shaped to give room for the screws 4, and to enable easy insertion of the washer into to washer space. The adapter module has a circumferential surface 30 between the first and second sides 20, 22, being an outer surface that connects the first and second sides to each other.

Preferably, the module has an essentially circular cylindrical shape.

Figure 3:
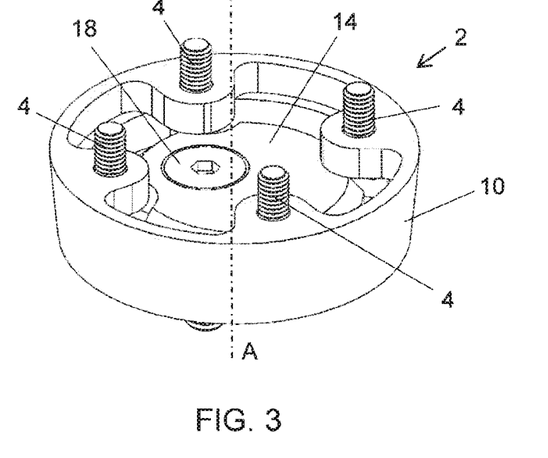
FIG. 3 is a perspective illustration of the adapter module according to one embodiment of the present invention.
Figure 6:
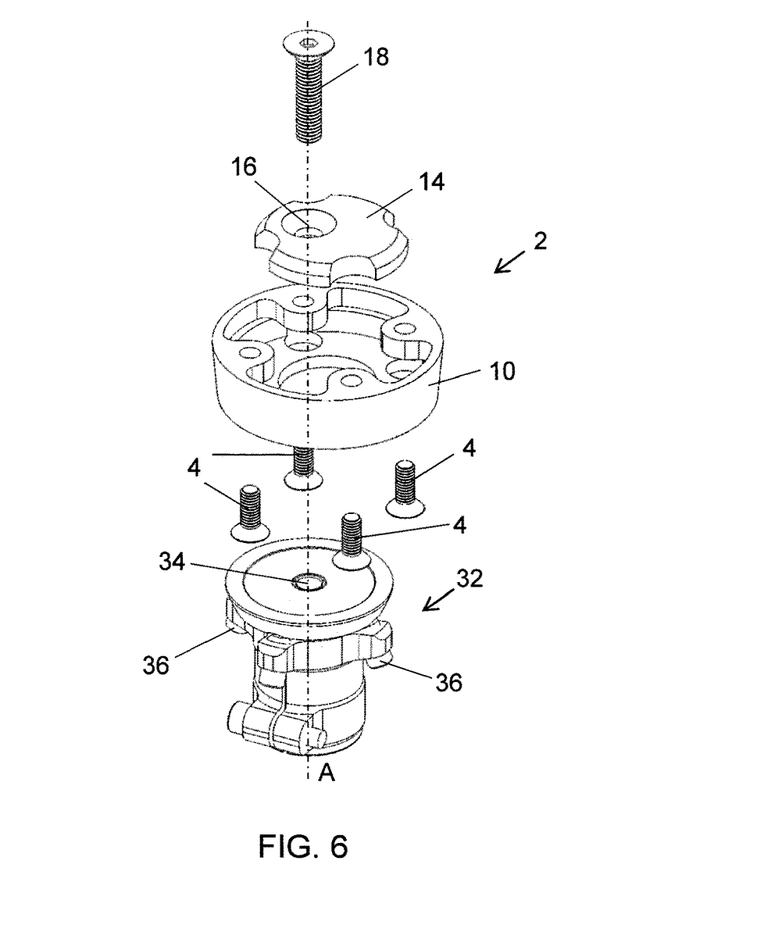
FIG. 6 shows an exploded view of the adapter module in combination with an angle adjustment module (tube clamp adaptor).

FIG. 3 shows the adapter module according to one embodiment provided with a module body that holds the connection washer in a washer space while still allowing the four attachment screws to connect the adapter module to the socket member. This allows attachment via the attachment screw to attach several other prosthetic components, where one is shown in FIG. 6. As the connection washer is movable within the module body in a plane perpendicular to axis A, the required adjustments are possible to achieve.

With references to FIGS. 6-12 a prosthesis arrangement according to further embodiments are illustrated. It is in particular referred to FIGS. 6 and 7.

The prosthesis arrangement comprises the adapter module 2 that has been described above with references to FIGS. 3-5, and an angle adjustment module 32 structured to be attached to the adapter module. The angle adjustment module is provided with a threaded hole 34 for cooperation with the washer attachment screw, by screwing the attachment screw into the hole. In an alternative embodiment, as discussed above, the angle adjustment module is structured to receive the attachment screw head and the screw extends through a non-threaded hole along axis A such that the threaded end of the attachment screw may be attached to the threaded through-going first opening of the connection washer.

Figure 7:
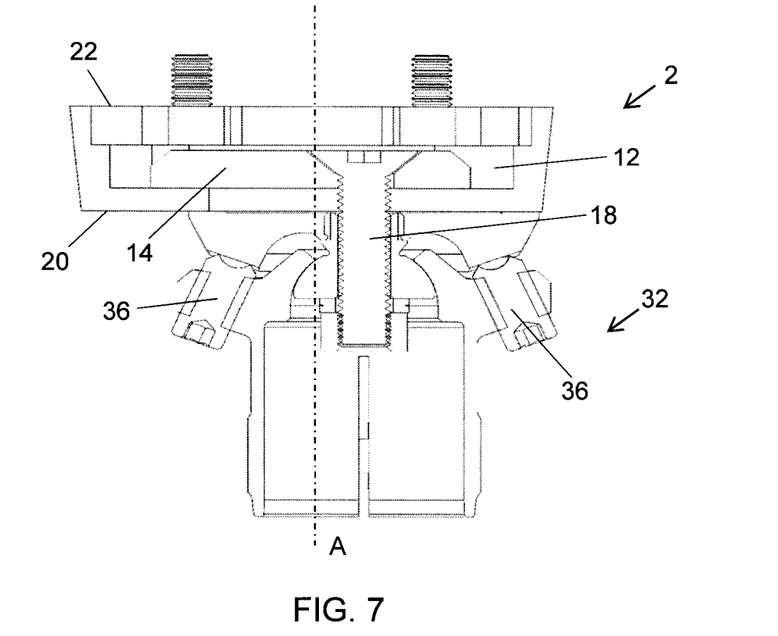
FIG. 7 shows a cross-sectional view of the adapter module with the angle adjustment module (with a tube clamp adaptor with angle adjustment).
Figure 8:
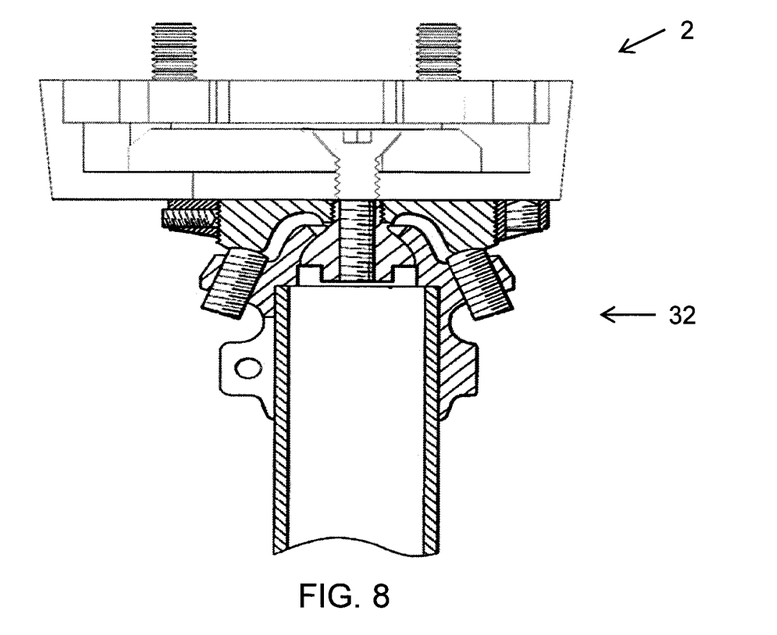
FIGS. 8-12 illustrate various examples of prosthetic arrangements according to the present invention.
Figure 9:
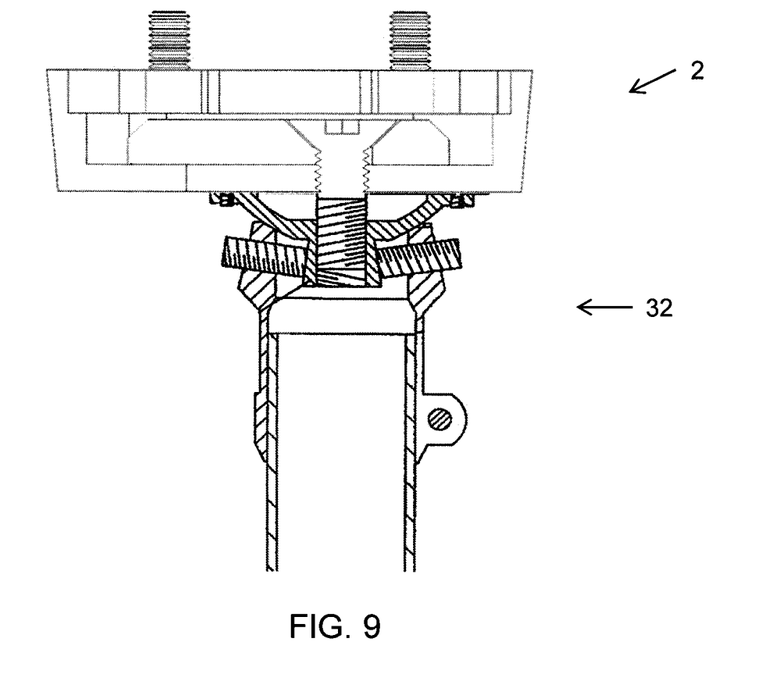
Figure 10:
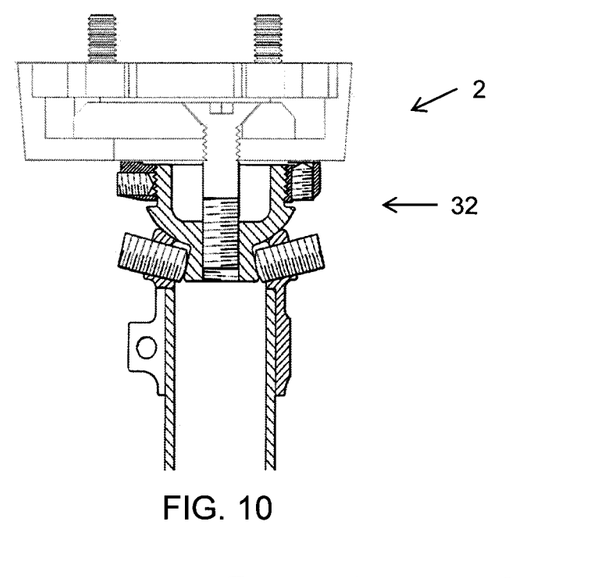

The angle adjustment module is provided with adjustment members 36, e.g. set screws, to adjust the angle of a prosthesis member attached to the angle adjustment module in the sagittal plane and in the frontal plane. Thus, the angle adjustment module provides means for adjusting the angle of the prosthesis in two perpendicular planes. More in detail, when a correct position is set in one plane this position is kept, i.e. does not change, when the correct position is set in the other plane. Thus, the angle adjustments may be performed independently in the two different planes.

The locking in a correct position may also be achieved by an outer locking ring (not shown) provided at the angle adjustment module that enables adjustments of angles. Thus, angle adjustments and also rotational and translational positional changes may be performed without having to divide the prosthesis. The locking ring may also provide the adjustment module one further adjustment dimension by including features to adjust the length in the distal direction.

The angle adjustment module may be provided with a square stud similar to the one illustrated in FIGS. 1 and 2 and having the form of a cut four sided pyramid, divergently extending from the base. Set screws are then applied for cooperation with the sides of the stud structured to adjust the angle between the prosthesis and the longitudinal direction of the stud. See e.g. U.S. Pat. Nos. 5,888,233 and 6,398,817.

The angle adjustment module may also be provided with a sphere arranged at a support plate. The sphere is structured to slide against an internally spherical surface when the angle is adjusted by use of the set screws. The set screws have an angled direction in relation to the support plate. When all set screws are fixated the angle is locked. See e.g. U.S. Pat. No. 5,013,325.

Figure 11:
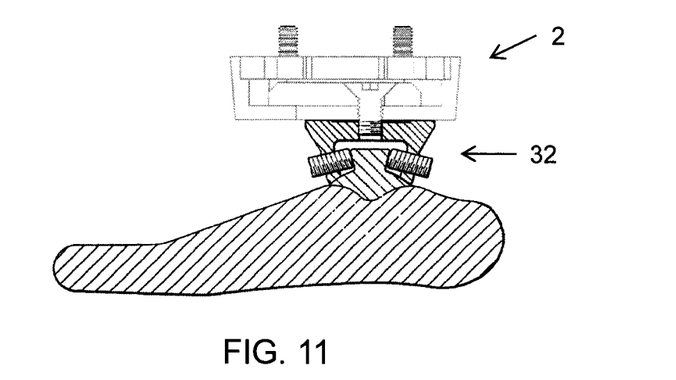
Figure 12:
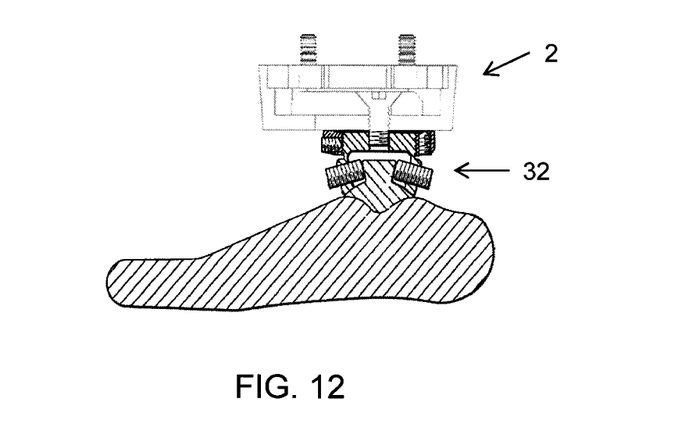

FIGS. 8-12 shows various examples of angle adjustment modules. In particular, FIGS. 11 and 12 show variations where the prosthesis arrangement is connected to a foot prosthesis.

The present invention is not limited to the above-described preferred embodiments.

Various alternatives, modifications and equivalents may be used. Therefore, the above embodiments should not be taken as limiting the scope of the invention, which is defined by the appending claims.

The invention claimed is:

1. A prosthetic adapter module configured to be attached, by a predetermined number of screws, to a socket member of a prosthetic sleeve, into which sleeve an amputation stump of a prosthesis user is to be inserted, the adapter module comprising:
   a disc-shaped connection washer having a central axis, and
   a module body provided with a washer space structured to provide room for the disc-shaped connection washer,
   the washer space having an extension to provide for movement of the disc-shaped connection washer within a plane essentially perpendicular to a longitudinal axis of said prosthetic sleeve prior to the disc-shaped connection washer being fixated in a determined position,
   the disc-shaped connection washer having an interior surface defining a through hole for receiving a washer attachment screw such that the screw essentially extends along said longitudinal axis,
   the through hole having a central axis centered with respect to the interior surface of the connection washer that defines the through hole,
   the central axis of the through hole being positioned off-center in relation to the central axis of the disc-shaped connection washer in order to maximize lateral movement of the disc-shaped connection washer in all directions within the plane,
   the module body being provided with a first side structured to face the socket member, and a second side at the other side of the module body, and
   the first side being provided with a first side opening to the washer space having a size such that the disc-shaped connection washer may enter the washer space via the first side opening.

2. The prosthetic adapter module according to claim 1, wherein said washer attachment screw extends in a direction away from the amputation stump.

3. The prosthetic adapter module according to claim 1, wherein said first side is provided with a predetermined number of through-going holes structured to receive said screws for attachment of said adapter module to said socket member.

4. The prosthetic adapter module according to claim 1, wherein said second side is provided with a through-going second side opening through which second side opening the washer attachment screw extends, and wherein the second side opening has a width in a direction perpendicular to the longitudinal axis of the screw that is larger than the outer diameter of the screw, but smaller than the diameter of the disc-shaped connection washer.

5. The prosthetic adapter module according to claim 1, wherein the adapter module is provided with a circumferential surface between said first and second sides, and wherein the module has an essentially circular cylindrical shape.

6. A prosthesis arrangement comprising a prosthetic adapter module configured to be attached, by a predetermined number of screws, to a socket member of a prosthetic sleeve, into which sleeve an amputation stump of a prosthesis user is to be inserted, the adapter module comprising:
   a disc-shaped connection washer having a central axis, and
   a module body provided with a washer space structured to provide room for the disc-shaped connection washer,
   the washer space having an extension to provide for movement of the disc-shaped connection washer within a plane essentially perpendicular to a longitudinal axis of said prosthetic sleeve prior to the disc-shaped connection washer being fixated in a determined position,
   the disc-shaped connection washer having an interior surface defining a through hole for receiving a washer attachment screw such that the screw essentially extends along said longitudinal axis,
   the through hole having a central axis centered with respect to the interior surface of the connection washer that defines the through hole, and
   the central axis of the through hole being positioned off-center in relation to the central axis of the disc-shaped connection washer in order to maximize lateral movement of the disc-shaped connection washer in all directions within the plane; and
   wherein the arrangement further comprises an angle adjustment module structured to be attached to said adapter module, and wherein said angle adjustment module is provided with a threaded hole for cooperation with said washer attachment screw.

7. The prosthesis arrangement according to claim 6, wherein said angle adjustment module is provided with adjustment members to adjust the angle of a prosthesis attached to the angle adjustment module in the sagittal plane and in the frontal plane.

8. The prosthetic adapter module according to claim 1, wherein the interior surface of the disc-shaped connection washer, and thus the through hole in the disc-shaped connection washer, is circular.

9. The prosthetic adapter module according to claim 1, wherein the module body is provided with a through hole through which the washer attachment screw can extend to an adjustment module of the prosthetic limb device.

* * * * *